(12) United States Patent
O'Connor et al.

(10) Patent No.: US 11,779,488 B2
(45) Date of Patent: Oct. 10, 2023

(54) COOLING AND REFRIGERATION BASED ON VACUUM-DRIVEN WATER EVAPORATION

(71) Applicant: ArktiKus LLC, Andover, MA (US)

(72) Inventors: John P. O'Connor, Andover, MA (US); Cindy A. O'Connor, Andover, MA (US); Ellen E. Sheets, Boston, MA (US)

(73) Assignee: Arktikus LLC, Andover, MA (US)

( * ) Notice: Subject to any disclaimer, the term of this patent is extended or adjusted under 35 U.S.C. 154(b) by 334 days.

(21) Appl. No.: 16/845,943

(22) Filed: Apr. 10, 2020

(65) Prior Publication Data

US 2020/0323682 A1    Oct. 15, 2020

Related U.S. Application Data

(60) Provisional application No. 62/969,876, filed on Feb. 4, 2020, provisional application No. 62/880,189, filed
(Continued)

(51) Int. Cl.
*A61F 7/00* (2006.01)
*A61B 18/02* (2006.01)
(Continued)

(52) U.S. Cl.
CPC ........ *A61F 7/0085* (2013.01); *A61B 18/0218* (2013.01); *A61F 7/12* (2013.01);
(Continued)

(58) Field of Classification Search
CPC ...... A61B 18/0218; A61B 2018/00291; A61B 2018/00464; A61B 2018/00482;
(Continued)

(56) References Cited

U.S. PATENT DOCUMENTS

| 2,069,359 A | 2/1937 | Dudley |
| 3,423,950 A | 1/1969 | Reynolds |

(Continued)

FOREIGN PATENT DOCUMENTS

| CA | 2849828 A1 | 10/2015 |
| CN | 202133306 U | 2/2012 |

(Continued)

OTHER PUBLICATIONS

Ichiro Aoki, Analysis of characteristics of water flash evaporation under low-pressure conditions, Heat Transfer: Asian Research 29 (1) 2000, pp. 22-33, DOI: 10.1002/(SICI)1523-1496(200001)29:13. 3.CG;2-M (Dec. 1999).

(Continued)

*Primary Examiner* — Tigist S Demie
(74) *Attorney, Agent, or Firm* — David E. Boundy; Potomac Law Group, PLLC

(57) ABSTRACT

Apparatus for cooling an object, space, or tissues of a patient. A vacuum chamber is designed to be placed in thermal contact with the object or space to be cooled, or against a patient to be treated. A water sprayer is configured to spray water into the vacuum chamber or against a cooling wall of the chamber. A vacuum pump and control are designed to maintain vacuum below ambient pressure in the vacuum chamber sufficient to cause accelerated evaporation of the water and cooling to a temperature desired for cooling of the object, space, or patient.

30 Claims, 6 Drawing Sheets

Related U.S. Application Data on Jul. 30, 2019, provisional application No. 62/859,767, filed on Jun. 11, 2019, provisional application No. 62/832,257, filed on Apr. 10, 2019.

(51) Int. Cl.
*A61F 7/12* (2006.01)
*F24F 5/00* (2006.01)
*A61B 18/00* (2006.01)

(52) U.S. Cl.
CPC .. *F24F 5/0035* (2013.01); *A61B 2018/00541* (2013.01); *A61B 2018/00577* (2013.01); *A61F 2007/0052* (2013.01); *A61F 2007/0063* (2013.01); *A61F 2007/0068* (2013.01)

(58) Field of Classification Search
CPC ........... A61B 2018/00541; A61B 2018/00577; A61B 2018/0212; A61F 2007/0052; A61F 2007/0063; A61F 2007/0068; A61F 2007/0069; A61F 2007/0239; A61F 7/0085; A61F 7/12; F24F 5/0035; Y02B 30/54

See application file for complete search history.

(56) References Cited

U.S. PATENT DOCUMENTS

| | | | |
|---|---|---|---|
| 5,423,807 | A | 6/1995 | Milder |
| 6,257,011 | B1 | 7/2001 | Siman-Tov |
| 6,865,825 | B2 | 3/2005 | Bailey |
| 7,077,858 | B2 | 7/2006 | Fletcher |
| 7,093,455 | B2 | 8/2006 | Holtzapple |
| 7,367,341 | B2 | 5/2008 | Anderson |
| 7,721,349 | B1 | 5/2010 | Strauss |
| 7,842,029 | B2 | 11/2010 | Anderson |
| 8,907,594 | B2 | 12/2014 | Begg |
| 9,241,826 | B1* | 1/2016 | Shih .................. A61B 17/1325 |
| 9,522,031 | B2 | 12/2016 | Anderson |
| 9,855,166 | B2 | 1/2018 | Anderson |
| 10,085,881 | B2 | 10/2018 | Karnik |
| 2009/0234325 | A1 | 9/2009 | Rozenberg |
| 2013/0030411 | A1* | 1/2013 | Kreck ............... A61M 16/0409 607/105 |
| 2013/0233000 | A1 | 9/2013 | Hodgson |
| 2014/0116081 | A1 | 5/2014 | Ritchie |
| 2014/0276539 | A1* | 9/2014 | Allison .................. A61N 1/403 607/101 |
| 2014/0343542 | A1 | 11/2014 | Karnik |
| 2015/0297279 | A1 | 10/2015 | Clarke |
| 2017/0089618 | A1 | 3/2017 | Coppola |
| 2018/0289538 | A1 | 10/2018 | Velis |
| 2018/0317344 | A1* | 11/2018 | Parnes ..................... G06F 1/20 |
| 2019/0053939 | A1 | 2/2019 | Garibyan |
| 2020/0054482 | A1 | 2/2020 | Manstein |

FOREIGN PATENT DOCUMENTS

| | | |
|---|---|---|
| CN | 109489160 A | 3/2019 |
| WO | WO2015/115688 | 6/2015 |
| WO | WO2018/136830 | 7/2018 |
| WO | WO2018/152068 | 8/2018 |
| WO | WO2018/160797 | 9/2018 |

OTHER PUBLICATIONS

Elsevier Science Direct, Vacuum Evaporation.
Geerlofs, Vacuum Cooler.
Eric L. Golliher, et al., Development of the Compact Flash Evaporator System for Exploration, SAE Technical Paper Series 2007-01-3204, 37th International Conference On Environmental Systems, Chicago Illinois, doi 10.4271/2007-01-3204 (Jul. 9-12, 2007).
Eric L. Golliher, Compact Flash Evaporator System Developed NASA Glenn 2007, from 2007 Research & Technolgy, National Aeronautics and Space Administration (pp. 87-88).
Eric L. Golliher, et al., Testing of a Compact Flash Evaporator System for Exploration, SAE Technical Paper Series 2008-01-2167, 38th International Conference on Environmental Systems, San Francisco, California, doi 10.4271/2008-01-2167 (Jun. 29-Jul. 2, 2008).
Eric L. Golliher, et al., Exploration of Impinging Water Spray Heat Transfer at System Pressures Near the Triple Point, Proceedings of the 2013 International Mechanical Engineering Congress & Exposition IMECE2013, Nov. 15-21, 2013, San Diego, California, USA DOI 10.1115/IMECE2013-66872.
Anabel Marcos et al., Spray Cooling At Low System Pressure, 18th IEEE Semi-Therm Symposium, 169-175, 10.1109/STHERM.2002.991364 (2002).
Michele Marcotte, Stefan Grabowski, Minimising energy consumption associated with drying, baking and evaporation, Handbook of Water and Energy Management in Food Processing Woodhead Publishing Series in Food Science, Technology and Nutrition, 2008, pp. 481-522.
Bonnie J. McBride et al., NASA Glenn Coefficients for Calculating Thermodynamic Properties of Individual Species, NASA/TP-2002-211556 (Sep. 2002).
Chao Wang, Ruina Xu, Yu Song, Peixue Jiang, Study on water droplet flash evaporation in vacuum spray cooling, International Journal of Heat and Mass Transfer 112 (2017) 279-288, DOI: 10.1016/j.ijheatmasstransfer.2017.04.111 (Sep. 2017).
PCT/IB2020/053449, PCT/ISA/210, International Search Report (dated Jul. 15, 2020).
PCT/IB2020/053449, PCT/ISA/237, Written Opinion of the International Searching Authority (dated Jul. 15, 2020).
Ichiro Aoki, Analysis of characteristics of water flash evaporation under low-pressure conditions, Heat Transfer: Asian Research 29 (1) 2000, pp. 22-33, DOI: 10.1002/(SICI)1523-1496(200001)29:13. 3.CO;2-M (Dec. 1999).
Claire J. Proudfoot, et al., Analgesia Mediated by the TRPM8 Cold Receptor in Chronic Neuropathic Pain, Current Biology 16, 1591-1605, DOI: 10.1016/j.cub.2006.07.061 (Aug. 22, 2006).
Andy D. Weyer and Sonya G. Lehto, Development of TRPM8 Antagonists to Treat Chronic Pain and Migraine, Pharmaceuticals (Basel) 2017, 10, 37; doi:10.3390/ph10020037 (Mar. 30, 2017).
EP 20787730.9, Form 1507S, Extended European Search Report (dated Dec. 12, 2022).

* cited by examiner

COOLING AND REFRIGERATION BASED ON VACUUM-DRIVEN WATER EVAPORATION

This application is a non-provisional of U.S. Provisional Ser. No. 62/969,876, filed Feb. 4, 2020, titled "Cooling and Refrigeration Based on Vacuum-Driven Water Evaporation," a non-provisional of U.S. Provisional Ser. No. 62/880,189, filed Jul. 30, 2019, titled "Cooling and Refrigeration Based on Vacuum-Driven Water Evaporation," a non-provisional of U.S. Provisional Ser. No. 62/859,767, filed Jun. 11, 2019, titled "Cooling and Refrigeration," and a non-provisional of U.S. Provisional Ser. No. 62/832,257, filed Apr. 10, 2019, titled "Cooling of Tissue," all of which are incorporated herein by reference.

BACKGROUND

This application relates to cooling and refrigeration based on vacuum-driven water evaporation.

SUMMARY

In general, in a first aspect, the invention features a method. A vacuum chamber is placed against tissues of the patient for which cooling is desired for medical treatment. Water is sprayed from a mister into the vacuum chamber or against a cooling wall of the vacuum chamber. Vacuum is maintained in the vacuum chamber sufficient to cause accelerated evaporation of the water and cooling to a temperature desired for cooling of tissues of the patient.

In general, in a second aspect, the invention features apparatus for treating a patient. A vacuum chamber has a cooling wall designed to be placed against tissues of the patient for which cooling is desired for treatment. A water sprayer is designed to spray water into the vacuum chamber. A vacuum pump and control are designed to maintain vacuum in the vacuum chamber sufficient to cause accelerated evaporation of the water and cooling to a temperature desired for cooling of tissues of the patient.

In general, in a third aspect, the invention features a method of cooling an object or space. A vacuum chamber is placed in thermal contact with tissue, an object, or space to be cooled. Water is sprayed from a mister into the vacuum chamber. Vacuum below room ambient pressure is maintained in the vacuum chamber sufficient to cause accelerated evaporation of the water and cooling of the tissue, object, or space to a desired temperature below its ambient temperature.

In general, in a fourth aspect, the invention features apparatus for cooling an object or space. A vacuum chamber has a cooling wall designed to be placed against the object or space to be cooled. A water sprayer is configured to spray water into the vacuum chamber or against the cooling wall. Apparatus is designed to maintain vacuum below ambient pressure in the vacuum chamber sufficient to cause accelerated evaporation of the water and cooling of the cooling wall to a temperature desired for cooling of the object or space.

Embodiments of the invention may include one or more of the following features. These features may be used singly, or in combination with each other. The vacuum chamber may be formed as open vacuum bell open on a side to be sealed to the tissue, object, or space. The vacuum chamber may be formed as an enclosed volume having a cooling wall at one side, and the cooling wall may be designed to be placed in physical contact with the object, space, or tissues of the patient. The vacuum chamber may be formed as a vacuum bell sealed to a flat thermally conductive platen, and the platen may be designed to be placed in thermal contact with the tissue, object, or space. The platen may be coated with a non-metallic nonstick release material designed to prevent adhesion and resultant tissue damage resulting from freezing of the tissue to be cooled or water between the tissue and the platen. The water may hold in solution an electrolyte chosen to depress freezing point of the water to a desired temperature. The vacuum chamber may include one or more thermal sensors. Vacuum may be controlled by a computer designed to obtain thermal data from the one or more thermal sensors, and to control one or more of water flow rate, vacuum pressure, and electrolyte solution, to control for a desired temperature and/or rate of cooling, and/or to correct for various confounders in thermal flow into the vacuum chamber. The tissue to be cooled may be tissue of a human patient, such as adipose tissue, skin, cancerous tissue, malignant cells, undesired benign cells that are selectively sensitive to cold, or goblet cells. The cooling treatment may be for purposes of disrupting fat, to reduce pain, to lighten skin and/or to reduce hypopigmentation, or to ablate undesired tissue. The tissue may be skin, in the gastrointestinal tract, or in the respiratory tract. The cooling may be designed to disrupt undesired cells. The space to be cooled may be an enclosed space to be cooled to refrigeration or freezing temperatures. The space to be cooled may be a room to be cooled to air conditioning temperatures.

The above advantages and features are of representative embodiments only, and are presented only to assist in understanding the invention. It should be understood that they are not to be considered limitations on the invention as defined by the claims. Additional features and advantages of embodiments of the invention will become apparent in the following description, from the drawings, and from the claims.

DESCRIPTION

Figure 1A:
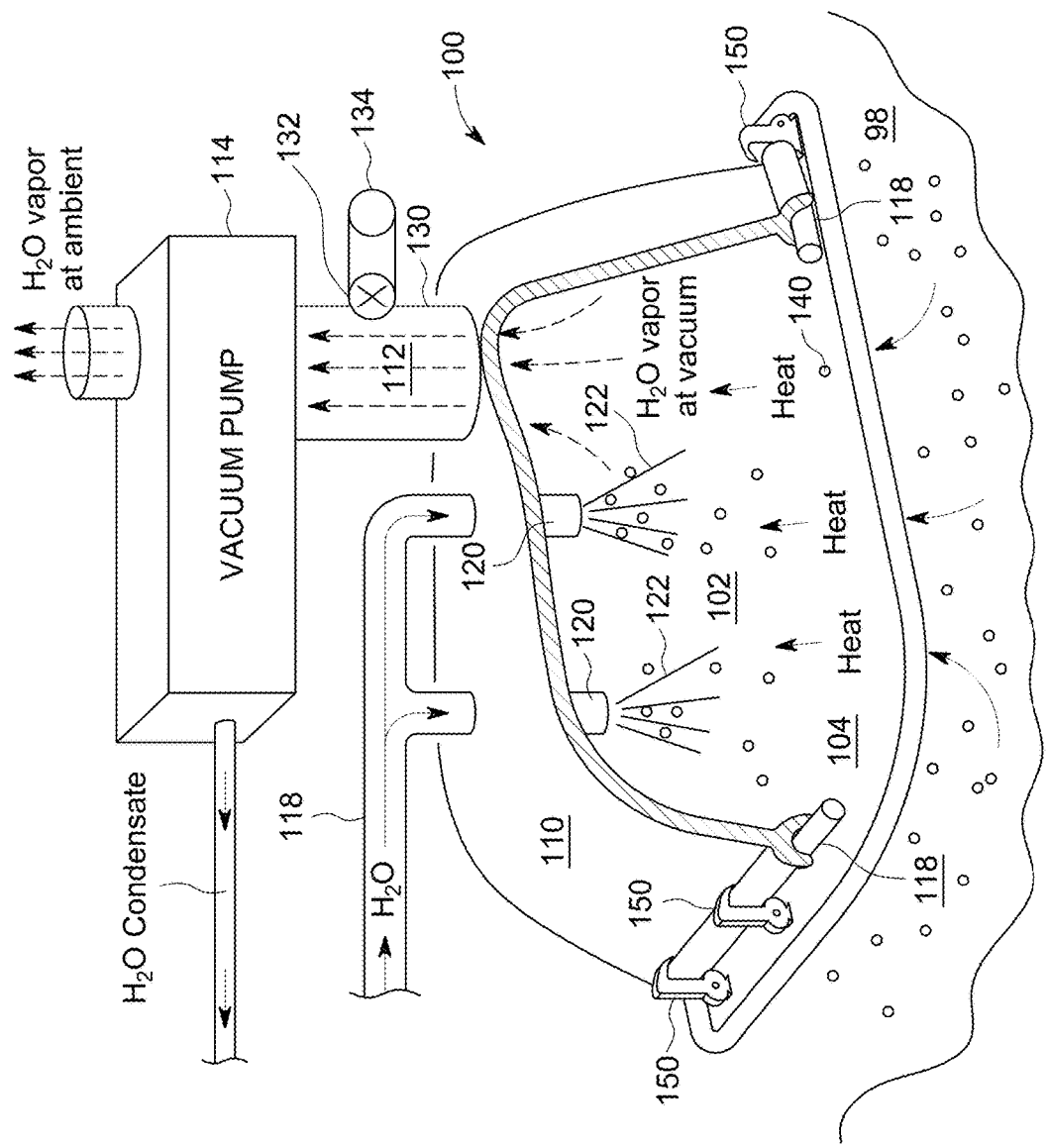
FIG. 1A is a perspective view, partially cut away, of a cooling apparatus.

The Description is organized as follows.

I. Introduction and Overview
II. Apparatus for Vacuum-Driven Evaporative Cooling
   II.A. Vacuum Bell Sealing Against the Skin
   II.B. Electrolyte Solutions as Coolant
III. Application as a Refrigeration or Air Conditioning System
IV. Cooling for Medical and Therapeutic Applications
   IV.A. Cryolipolysis
   IV.B. Vacuum Bell Sealing Against the Skin
   IV.C. Cooling for Analgesia
   IV.D. Cooling for Hypopigmentation IV.E. Cooling for Pharmaceutical Transportation Cold Chain
IV.F. Cooling for Tissue Within the Body
V. Embodiments I. Introduction and Overview Referring to FIGS. 1A and 1B, a vacuum cooling apparatus 100 may be used to cool a selected region 98 by vaporization of a liquid, especially a liquid with a high enthalpy of vaporization, for example, water. Vaporization, and thus cooling, may be accelerated and controlled by applying vacuum above the liquid. A vacuum chamber 102 may be formed as an enclosed volume 102 with a conductive side 104 for providing cooling to the selected region, and apparatus 100 may be arranged to effect evaporation or sublimation of the water against that thermally-conductive side 104. A vacuum may be drawn in vacuum chamber 102 that drives evaporation or sublimation of the liquid. The energy required to provide the heat of vaporization is drawn through thermally-conductive side wall 104 of vacuum chamber 102, thus lowering the temperature of conductive side 104, which in turn cools whatever 98 is on the other side of that conductive wall. Vacuum in chamber 102 drives the vaporization of the coolant, and then the heat of vaporization is pulled from the subject 98 to be cooled.

Convection, such as a column of moving air, may be used to move the cooling to desired regions. With an appropriate electrical and vacuum pump arrangement, the device may be controlled to generate a controlled and precise drop in temperature of the conductive plate and hence of region 98 to be cooled to a desired level.

Apparatus 100 may enable thermal contact between the cooled conductive element with tissue to provide desired cooling of the tissue to specified temperatures. Selected regions 98 of tissue of a body may be cooled for various diagnostic or therapeutic purposes.

Figure 1B:
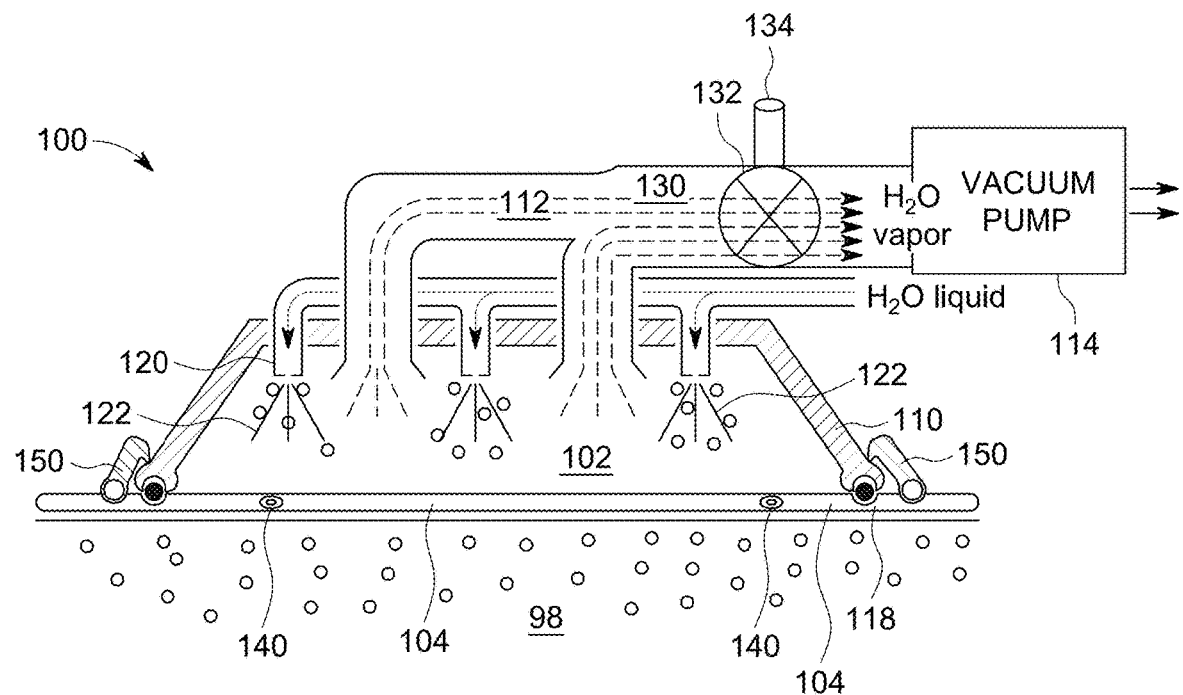
FIGS. 1B and 1C are schematic section views of a cooling apparatus.
Figure 1C:
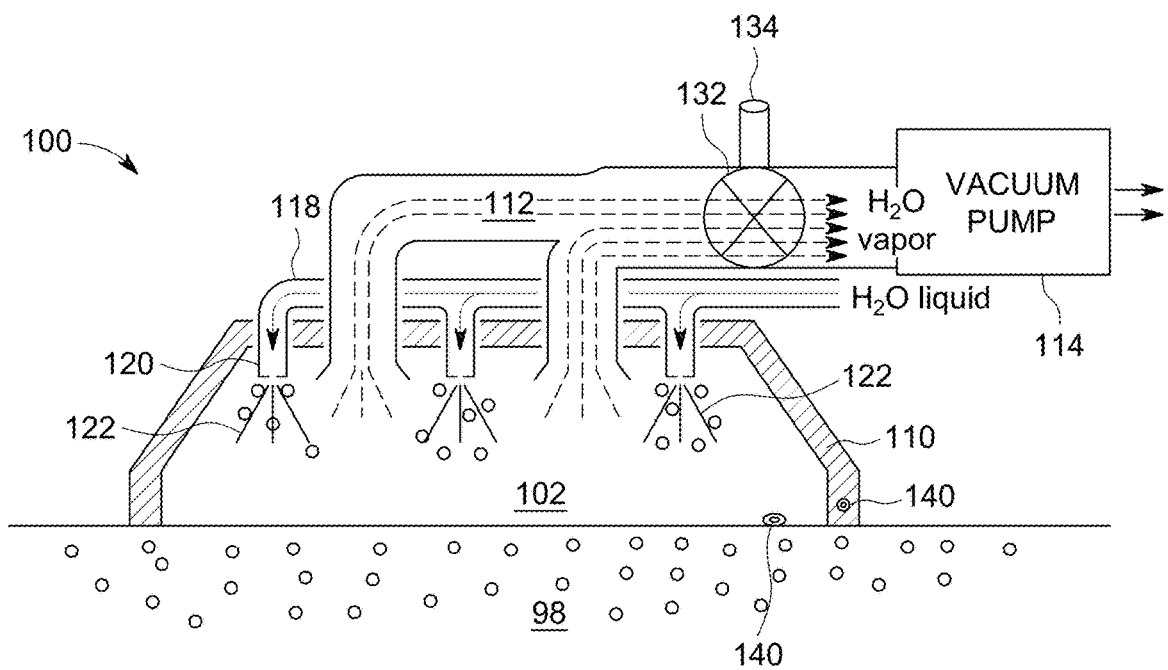

Referring to FIG. 1C, vacuum chamber 102 may be formed by a bell that seals against the skin 98, and apparatus 100 may be arranged to effect evaporation at the surface of the skin. A vacuum is drawn in vacuum chamber 102 that drives evaporation of the liquid. The energy required to provide the heat of vaporization is drawn from the tissue. As a result, energy is removed from the tissue and the tissue is cooled. With an appropriate electrical and vacuum pump arrangement 112, the device is controlled to generate a controlled and precise drop in temperature of tissue 98. In this way, certain tissue, such as adipose tissue, may be disrupted to provide a pathway for reabsorption of the tissue by the body and elimination of such tissue. In cases where there is no platen 104 to carry thermal sensors 140, sensors may be placed on the surface of the object 98 to be cooled, or in the wall of vacuum bell 110, or elsewhere.

This refrigeration/cooling apparatus may be used for a variety of purposes: food storage, medical therapies, pharmaceutical transportation cold-chain, and the like.

II. Apparatus for Vacuum-Driven Evaporative Cooling

Referring to FIGS. 1A and 1B, vacuum-driven evaporative cooling may provide desired cooling in a rapid and controlled manner. A vacuum bell 110 may placed in contact with a thermally conductive platen 104, and sealed to platen 104 at edges through the use of an O-ring or similar seal 118 around edge of thermally-conductive platen 104. Seal 118 prevents or reduces leaking of air into volume 102 enclosed between platen 104 and vacuum bell 110, and may provide thermal insulation between thermally conductive platen 104 and vacuum bell 110.

A spray device 120 may provide a spray or mist of liquid 122, preferably a liquid with a high specific heat of vaporization such as water, that is applied to the outer surface of thermally-conductive platen 104 within volume 102 between platen 104 and vacuum bell 110. A vacuum may be drawn into volume 102 by a suitable vacuum pump 114 connected to vacuum bell 110 through a gas conductive region such as a hose or pipe 130 through a three-way valve 132. As a result of the vacuum within the enclosure, liquid 122 within volume 102 will vaporize and become a gas, that is, water vapor if the liquid selected is water. The energy to vaporize the liquid is removed from conductive platen 104. The energy of the platen 104 is lowered and hence the temperature of the platen is lowered. This in turn cools tissue or region 98. Three-way valve 132 is used to connect to vacuum pump 114 or air inlet 134 to provide either vacuum suction from vacuum pump 114 or venting of chamber 102 using air inlet 134.

Water may be selected as the liquid to be misted and then vaporized within chamber 102. Due to the high vaporization energy of water (2,256 kilojoules per kilogram), a significant amount of heat may be removed from thermally conductive platen 104.

To provide a controllable method of heat removal, sensors such as thermocouples or RTDs (resistance thermometer detectors) 140 may be embedded within thermally conductive platen 104. These sensors may be monitored in real time by a control system such as a computerized analysis system. By measuring the temperatures of platen 104 during the vaporization process, it is possible to determine the heat flux leaving platen 104 and ensuring the desired temperatures of platen 104 are achieved and maintained during the vacuum-driven evaporative cooling process. With appropriate sensors, electronics, and control systems, it is possible to control temperature, temperature reduction of the platen, rate of cooling, and time. The controls may take into account various confounding factors such as the initial temperature of the region to be cooled and materials within the region to be cooled.

In one example implementation:
Mister 120 sprays water on to the back of conductive platen 104.
  The heat of vaporization of $H_2O$ is 2,256 joules per gram
Platen 104 may be formed of aluminum—aluminum has high thermal conductivity, but lower cost than, for example, silver.
  Dimensions: 10 cm×5 cm×0.5 cm
  Mass: 67.5 grams
  Specific heat 0.90 joules/gram/° C.
With vacuum applied to the box, the water vaporizes and draws heat from thermally-conductive platen 104.

To maintain the temperature of platen 104 at the selected temperature, additional small amounts of water may be sprayed and evacuated during the application period. The precise control of the misting and evacuation process may be determined by systemic unit testing and control algorithms included in the device based on the systemic unit testing that used the inputs from monitoring of sensors 140.

Any air remaining inside the vacuum volume may be managed, for example, to flow across the surface of platen 104 to enhance evaporation or sublimation. A fan may agitate this air, or vacuum draw 112 (and therefore exhaust of the water vapor) may be arranged at one side of the vacuum chamber and the inlet at the other, to provide relatively rapid changeover of the air volume, so that evaporation may be improved.

In some cases, the water vapor may be exhausted to the environment. In other cases, the water vapor may be recaptured, condensed, and recycled in a closed system.

Flash evaporation temperature is related to pressure as follows:

| temperature ° F./° C. | pressure (mbar/atm) |
| --- | --- |
| 70° F./21° C. | 25 mbar/0.024 atm |
| 65° F./18.3° C. | 20.5 mbar/0.020 atm |
| 60° F./15.6° C. | 17.4 mbar/0.017 atm |
| 50° F./10° C. | 12.5 mbar/0.012 atm |
| 41° F./5° C. | 8.7 mbar/0.0086 atm |
| 32° F./0° C. | 5.7 mbar/0.0056 atm |
| 14° F./−10° C. | 2.6 mbar/0.00257 atm |
| −4° F./−20° C. | 1.0 mbar/0.00099 atm |

From room temperature to freezing, the liquid/solid phase boundary is sufficiently close to log/linear that each ° C. in temperature reduction requires a reduction in pressure of just under 2%, more or less.

Platen 104 may be coated (on either the vacuum-facing side or the environment-facing side) with a coating material, typically a chemically-inert and thermally-conductive material. Thin coatings of Teflon, nylon, or some other plastic or resin, or some other non-metallic material, may be used. The coating may reduce adhesion and tissue damage during the cooling process. The coating may protect platen 104 if it is formed of a chemically-reactive material like aluminum.

The interior, vacuum-facing side of platen 104 may have fins, a highly-cavitated surface, or other surface features to increase surface area and evaporation rate.

In some cases, misted liquid 122, such as water, may have droplet diameters ranging from approximately 200 microns to 600 microns in diameter and as a result, the surface tension of the droplets will be sufficiently high to adhere to platen 104 at any orientation. In such cases, spray device 120 and platen 104 (and thus entire apparatus 100) may be oriented at any angle.

Components of the vacuum chamber may be sealed against each other by one or more O-rings 118. The material of the O-ring may be selected to provide low volatility into the vacuum, to seal well, and to provide good insulation between cooling platen 104 and vacuum bell 110. Good materials include various synthetic rubbers, such as Viton, a brand of high density FKM vinylidene fluoride fluoroelastomer material, from The Chemours Company.

Mister 120 may be a commercial mister, or a fuel-injection nozzle, or other spray device that emits finely-divided droplets and whose flow rate is easily and precisely controlled. Because evaporation rates are closely correlated to surface area of the droplets, finely divided droplets tend to be desirable.

The vacuum may be drawn by a commercial vacuum pump 114, available from companies such as Micropump, Inc. in Vancouver Wash., which in turn is part of IDEX Corp.

A microprocessor controller may be used to control various system parameters, principally (but not exclusively) water spray rate and vacuum pressure. The system parameters may be controlled moment-to-moment to:

maintain the surface temperature of platen 104 at the desired target temperature, as measured by temperature sensors 140 identify droplet icing, freezing, or fouling of the vacuum chamber, and reduce water mist rate until it's cleared or raise an alarm for the need for cleaning Control may be applied to water mist flow rate, power to the vacuum pump, opening of any pressure valves in the system, etc. Process control algorithms such as PID (proportional-integral-derivative controller) may be used to balance system parameters with perturbations in the environmental factors.

II.A. Vacuum Bell Sealing Against the Skin

Referring to FIG. 1C, in some cases, it may be useful to configure the vacuum chamber as an open-sided bell, with the object to be cooled providing the remaining side. This may be especially desirable when the cooling is to be applied to a part of the body. This is discussed in section IV.B, below.

II.B. Electrolyte Solutions as Coolant

In some cases, the evaporative liquid may be water, either purified or straight from the tap.

The use of saline may allow a lower freezing temperature to be obtained. An electrolyte such as sodium chloride or calcium chloride depresses freezing point, varying by concentration. The solute and concentration may be chosen to select a desired freezing point for the solution. The freezing point of water falls from 0° C. at 0% sodium chloride solution, to −12° C. at 15% (by mass) NaCl solution, to −17° C. at 20% solution, and maxes out at about −20° C. at 22% solution. −10° C. is a common temperature used to impact adipose cells in the body, reachable by a 13% (by mass) solution of NaCl. −18° C., a common temperature used for commercial freezer applications, is reachable with a NaCl solution of approximately 21% by mass. Calcium chloride solution may also be used. Calcium chloride has a lower freezing point than achievable with a sodium chloride solution. A 20% solution of CaCl freezes at −18° C., and a 30% solution of CaCl freezes at about −46° C.

Referring again to FIGS. 1A and 1B, if a saline solution is used, evaporation will leave behind a residue of salt on platen 104. For typical cooling cycles required to disrupt fatty tissues, less than a gram of sodium chloride or calcium chloride will be remain upon platen 104. To remove this material at the end of a cooling cycle, a set of quick connect units 150 are used to disconnect the conductive platen 104 and the non-conductive O-ring seal 118 from the vacuum bell 110. The interior surface of conductive platen 104 may then be wiped with a cloth containing water to remove the remaining sodium chloride or calcium chloride. The unit may then be simply reassembled using quick connect units 150 for the overall vacuum apparatus 100 to be ready for the next tissue cooling treatment.

III. Application as a Refrigeration or Air Conditioning System

Figure 2:
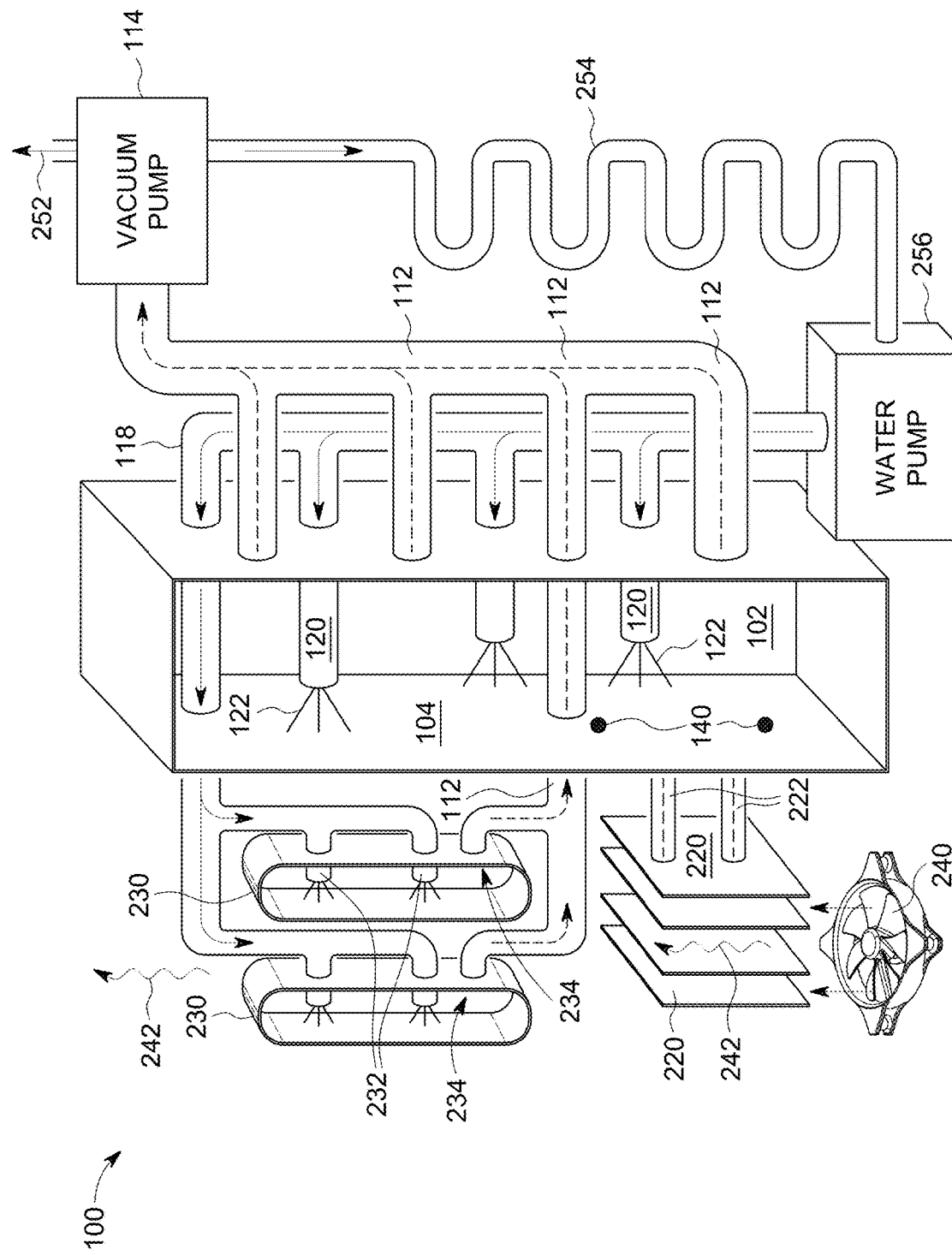
FIG. 2 is a perspective view, partially cut away, of a cooling apparatus.

Referring to FIG. 2, a refrigeration or air conditioning device 100 may use vacuum-driven evaporative cooling for air conditioning or refrigeration (in either case, lying at the left side of FIG. 2). A vacuum chamber 102 may be formed as an open space with spray misters 120 configured to spray 122 onto a conductive platen 104. Vacuum pump 114 may draw vacuum 112 into volume 102 facing platen 104. Thermal sensors such as thermocouples or RTDs 140 may be placed in platen 104 to monitor the heat flux and temperature of platen 104. Cooling fins 220 may be thermally connected to platen 140 by thermally conductive bars or by a convection cooling loop 222. Alternatively, multiple cooling chambers 230 may be provided, each having sprayers 232 and vacuum exhausts 234. Fins 220 or cooling chambers 230 may be either in, or in a duct for flow into, a cooled region which may in turn be an enclosed volume, such as a refrigerator or cold-chain chest for delivery of pharmaceuticals or other temperature-sensitive medical supplies or materials, or may be an open volume, such as a room to be air-conditioned.

As platen 104 or cooling chambers 230 are cooled due to the vaporization of liquid 122, a device 240, such as a fan, may force cooling air or air from the room to be cooled 242 to flow along the outer surface of platen 104, through fins 220, or past cooling chambers 230. Air flow 242 may be cooled and then directed to desired regions within the refrigeration device or to the room to be cooled.

Vacuum pump 114 may be situated exterior to the space for which cooling is desired. This allows the heat generated during operation of vacuum pump 114 to be dissipated into the ambient environment, without radiating back into the region where cooling is desired. The vapor generated from the vaporization of the liquid in the vacuum volume 102 may be exhausted 252 to the exterior of the desired region to be cooled, or may be forced through condenser 254 where the vapor is converted back to a liquid phase. The condensed liquid may then be recycled through water pump 256 to be sprayed through misters 120. This closed loop system does not release any of the coolant to the outside environment.

IV. Cooling for Medical and Therapeutic Applications

IV.A. Cryolipolysis

Referring again to FIGS. 1A, 1B, and 1C, cryolipolysis is a method for removing adipose tissue by cooling. The method involves controlled application of cooling within the temperature range of −11° C. to +5° C. Subcutaneous fat tissue is selectively sensitive to temperatures in this range. While the process is not fully understood; it appears that fatty tissue that is cooled below body temperature, but above the temperature at which tissue freezes, undergoes localized cell death ("apoptosis"), or the cells dissociate from the tissue matrix, followed by a local inflammatory response that gradually over the course of weeks to months results in elimination of the fat cells from the body, and thus a reduction of the fatty tissue layer. Cooling into this range tends to leave other cells, such as skin and nerve cells, undamaged. For example, overlying skin tolerates exposures to −10° C. for periods of a half hour to an hour without apparent damage. Cryolipolysis may be used as a noninvasive, localized reduction of fat deposits, reduce lipid-rich cells and fatty tissue, to reshape the contours of the body, for cosmetic or therapeutic reasons.

Vacuum-driven evaporative cooling apparatus 100 may provide desired cooling of tissues of the body in a rapid and controlled manner. Highly thermally conductive platen 104 coated with a thin layer of a non-metallic material may be placed in contact with desired region of tissue 98. The thin, nonconductive coating may prevent conductive platen 104 from adhering to tissue 98 when the temperature is lowered below 0° C., for example, because of freezing of water at the surface of the skin.

Computer control may read temperature sensors 140 and adjust water flow rate and vacuum pressure to control cooling to maintain a desired temperature and rate of cooling, to correct for various confounders such as variations in blood circulation that results in variations in supply of heat back into the tissue. Lower temperatures may be achieved by either lowering the vacuum pressure or adding electrolyte to the water being injected. Increased rate of cooling to a fixed destination temperature may be achieved by faster insertion of water and withdrawal of water vapor.

As an example of an application of this cooling process, the tissue may be cooled into the range where fat cells are selectively disrupted, and other tissues are not injured. In order to avoid frostbite, a specific temperature level and exposure may be determined, such as 45 minutes at −10° C. (14° F.), that injures the fat but not surrounding tissues. The system may be driven to apply the desired degree of cooling, to a layer of fat below the skin, typically 1 cm or a little more, per treatment.

The thermally-conductive platen may be flexible or conformal to allow platen 104 to conform to various body parts. A conformal platen may be constructed of multiple thin sheets of aluminum, each sheet polished smooth to allow the sheets to slip against each other with minimal lubricant so that the platen as a whole offers thermal conductivity approximating that of solid aluminum, but the whole stack sufficiently rigid to support vacuum.

In one example implementation:
Mister 120 sprays water on to the back of conductive platen 104.
Platen 104 may be formed of aluminum—aluminum has high thermal conductivity, but lower cost than, for example, silver.
Dimensions: 10 cm×5 cm×0.5 cm
Mass: 67.5 grams
Specific heat 0.90 joules/gram/° C.
Thin, non-conductive material may be a Teflon liner
Dimensions: 10 cm×5 cm×0.05 cm
Mass: 5.5 grams
Specific heat of Teflon: ~1.5 joules/gram/° C.
Tissue 98
Dimensions: 10 cm×5 cm×1 cm
Mass: 45 grams
Specific heat of tissue: 3.47 joules/gram/° C.

If tissue, Teflon and thermally-conductive platen begins at 37° C., the combined system drops ~10.0° C. per gram of water applied to platen 104. So, to have the tissue surface reach a target temperature −10° C., approximately 5 grams of water will need to be misted onto platen 104. This tissue surface temperature has been used in previous efforts with thermoelectric cooling systems to enable disruption of fatty tissue without damage to the skin surface of the tissue 98.

To account for blood flow heating, additional small amounts of water would be sprayed and evacuated during the application time period. The precise control of the misting and evacuation process would be determined by systemic unit testing and control algorithms included in the medical device based on the systemic unit testing that used the inputs from monitoring of sensors 140.

IV.B. Vacuum Bell Sealing Against the Skin

Referring again to FIG. 1C, a vacuum bell 110 may be placed in contact with desired region of tissue 98, without the intervening platen. Vacuum bell 110 may be sealed against tissue 98 via an O-ring, petroleum jelly, or similar sealant. Water spray mister 120 may provide a mist of water 122 directly to the outer surface of tissue 98 within the volume of the vacuum bell 110, and a vacuum pump 114 may draw vacuum 112 in volume 102 between vacuum bell 110 and tissue 98. If there is no platen 104, thermal sensors such as thermocouples or RTDs 140 may be placed on tissue surface 98. This approach may provide more rapid cooling, and is suitable where skin 98 is sufficiently thick and robust to tolerate applied vacuum and cooling without injury (for example, hemorrhaging or excessive evaporation). Where the skin or other tissue is less tolerant to vacuum, the platen approach of FIGS. 1A and 1B may be desirable.

IV.C. Cooling for Analgesia

As another example, the cooling may be used to provide analgesic effects to selected regions of the body.

Cooling tends to reduce the perception of pain. Cold therapy causes decreased nerve conduction velocity and other local effects to lessen the sense of pain perceived by peripheral nerves in the skin. Another conjectured mechanism of action is hypothesized: at the point where cold-sensing peripheral nerves reach the spinal cord, activation of cold-sensing receptors may interfere with pain-sensing nerves, reducing the perception of pain. Cooling one part of the body is known to reduce the perception of pain from elsewhere in the body. The effect seems to be larger for chronic pain such as arthritis, phantom-limb pain, or neuropathic pain. Cooling is also effective for pain of burns.

The vacuum-driven evaporative cooling device may be used to reduce pain by cooling specific portions of the body to specific temperatures, that vary with the part of the body and nature of the pain. Control systems of the device may be programmed to apply that level of liquid, e.g., water, and vacuum appropriate to apply the appropriate cooling for the patient's pain.

IV.D. Cooling for Hypopigmentation

As another example the cooling may be used to provide skin lightening to selected regions of the body.

Hypopigmentation has been observed as a side effect of temporary cooling or freezing of tissue. Loss of skin pigmentation may occur due decreased melanin production, decreased melanosome production, destruction of melanocytes, or inhibited transfer of melanosome into the keratinocytes in the lower region of the epidermal layer. While some hypopigmentation devices and systems have been developed, it may be desirable to effect improvements in this area. The methods and applications described herein may improve the consistency of the skin cooling or freezing and may improve the consistency of the duration of the skin freezing in a non-invasive manner. Such improvements may be desirable to improve overall hypopigmentation consistency.

IV.E. Cooling for Pharmaceutical Transportation Cold Chain

During transport of pharmaceuticals, blood products, organs for transplantation, or other temperature-sensitive medical supplies or materials, electrical power from a traditional stationary electrical source, such as an electrical outlet connected to the electrical grid, may be unavailable or inconvenient. Electricity for a cold transport chest may be provided by a portable power source, for example, solar cells that convert sunlight into electricity. A small transport cooling chamber that utilizes vacuum-driven vaporization is expected to consume approximately 40 to 60 watts. Sufficient electrical power may be provided by approximately 2,500 square centimeters of solar cells (5 kW/square meter/day as the solar flux). This array of solar cells may be configured as a square array of 50 cm on a side. Since this area is larger than a typical pharmaceutical transport container, foldable solar cells may be used. This may allow the solar cells to be folded together for ease of initial conveyance and then unfolded to acquire solar energy as needed during pharmaceutical transport. A switchable connection may allow the cooling system to be alternatively switched between the solar array and a traditional fixed-location power outlet.

IV.F. Cooling for Tissue Ablation Within the Body

Figure 3A:
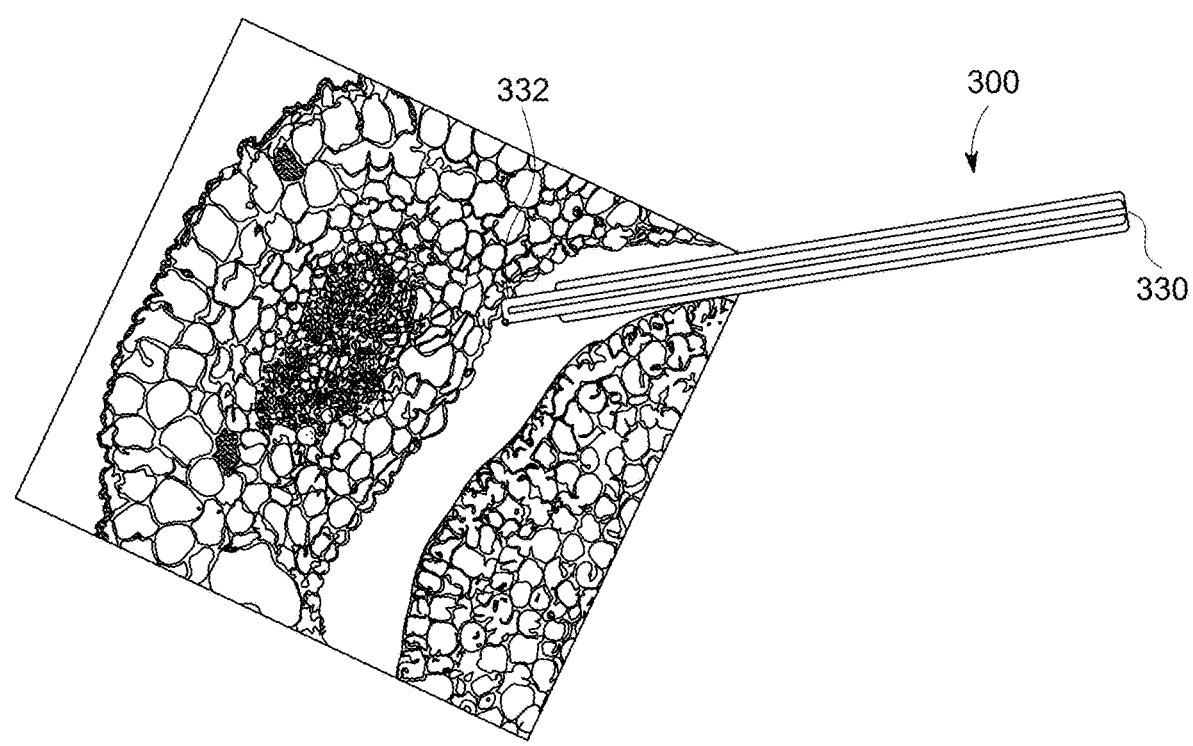
FIG. 3A is a section view of a body lumen being treated with a catheter.

Referring to FIG. 3A, tissue within the body may be cooled to ablate undesired cells from the tissue linings.

Figure 3B:
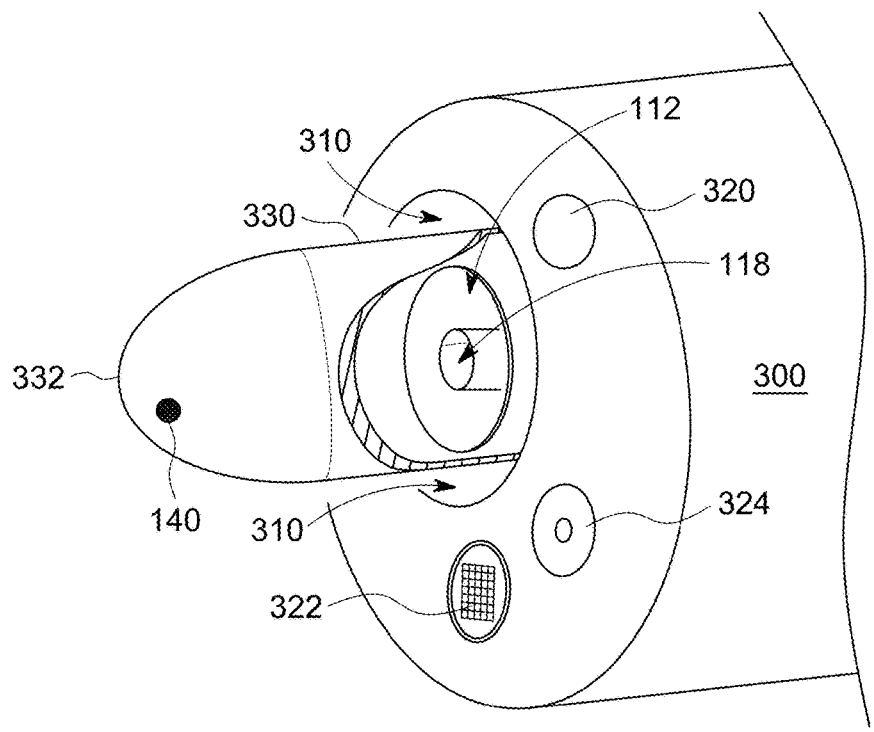
FIGS. 3B, 3C, and 3D are perspective views, partially cut away, of catheter tips.

Endoscope 300 may be inserted into the body through a natural orifice. For example, a bronchoscope may be advanced through the trachea to the selected generation of the lung, i.e., trachea, main bronchi, lobular bronchi, or segmental bronchi. Or a gastroscope may be advanced through the mouth to access the esophagus, stomach, duodenum, or small intestine. Referring to FIG. 3B, endoscope 300 may be selected to have the largest available working channel 310, e.g., for a 6 mm outer diameter bronchoscope with a 2 mm working channel to pass instruments through the bronchoscope or for the gastrointestinal tract, a 10 mm outer diameter endoscope with up to a 2.8 mm working channel to pass instruments through the scope.

Endoscope 300 may have an illumination source 320 and objective lens or CCD camera 322 that may allow the operator to visualize the passages within the body. Endoscope 300 may have air/water nozzle and/or water jet 324 features that permit the operator to clear undesired materials from the path of endoscope 300 to enhance navigation to the desired location within the body. When endoscope 300 is at the selected position within the body, a catheter 330 with multiple lumens may be passed through the working channel of the endoscope with the catheter tip extended a short distance beyond the tip of the endoscope. Catheter tip 332 may be a solid unit or an expandable member. It may be a conformal, highly thermal conductive material coated with a thin layer of a non-metallic material. Catheter tip 332 may then be placed in contact with the wall of the tissue at the selected position within the body. A specified amount, say 1 gram, of a liquid, e.g., water, is then injected into the catheter inner water-feed lumen 118, the liquid transport tube, by a suitable device (not shown) from outside of the body.

The liquid is advanced to the tip of the catheter where it accumulates in the outer vacuum-draw lumen 112. A vacuum is then applied to outer vacuum-draw lumen 112 of catheter 330 by the use of a vacuum pump (not shown). When an appropriate vacuum level is attained (roughly less than 10 Torr), the liquid will vaporize and tip 332 of the catheter outer lumen 112 (and the temperature of the tissue with which it is in contact) will cool significantly due to the absorption of the heat of vaporization from the tissue. A thermal sensor 140, e.g., a thermistor or thermocouple, is placed at tip 332 of outer vacuum-draw lumen 112 to measure the temperature of the impacted tissue to ensure the desired temperature is achieved by cooling.

By the appropriate selection of the volume of the liquid that is vaporized and the composition of the liquid (for example, water, sodium chloride solution, or calcium chloride solution), the tissue may be cooled to below −20° C. and within a controlled depth of the tissue (e.g., 1 to 5 mm depth). This may enable the ablation of undesired cells at the selected location, such as excessive goblet cells found with chronic bronchitis. Due to the nature of the cryobiology, the epithelium returns to normal epithelium following ablation, e.g., with the vast majority of the goblet cells eliminated from the bronchial tissue.

When the catheter is to be moved to the next location of the tissue to be cooled, a warm liquid or warm air may be passed through lumens 118, 112 the catheter to increase the temperature to a level where no damage to the tissue may be caused due to the catheter tip "sticking" to the tissue by freezing.

A sequence of cooling of the desired linings of tissues may enable normal epithelial tissue linings to return to the selected regions. This approach may be used, for example, in the airways to ablate segments of the segmental, lobular, main bronchi and the trachea may be employed to ablate the undesired cells, such as excessive goblet cells, from the selected bronchi with a return to normal epithelium in each location.

Figure 3C:
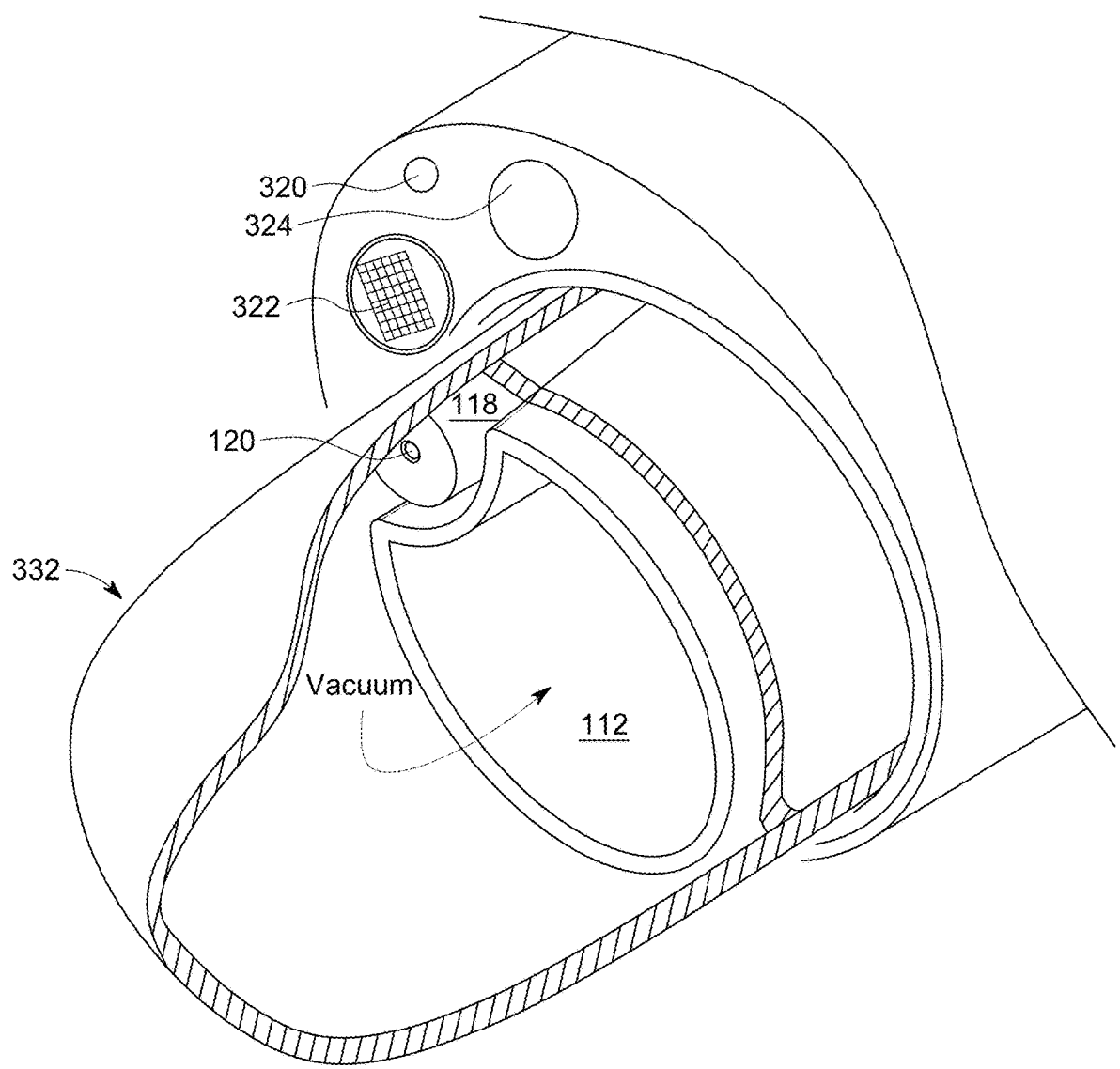
Figure 3D:
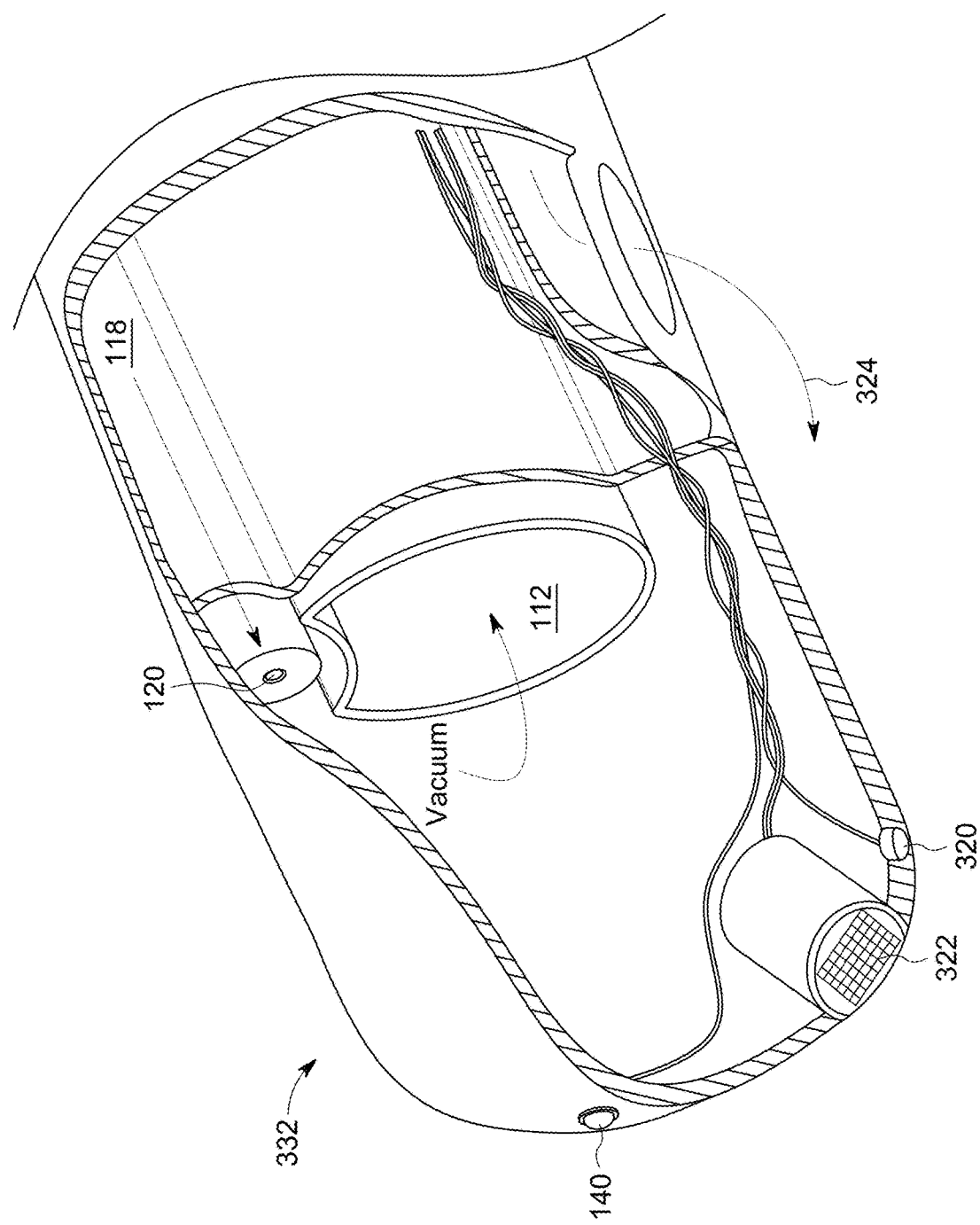

Referring to FIGS. 3C and 3D, both functions may be combined into a single catheter that provides vacuum-driven evaporative cooling, mechanical delivery, and endoscopic optical visibility to guide the cooling to the precise location at which treatment is to be provided. The tip of the catheter may be formed primarily of an aluminum or steel globe that supports vacuum. Vacuum may be drawn through a lumen acting as a vacuum-draw channel 112. A sprayer or mister 120 may spray water or a saline solution into the vacuum globe. A thermocouple or other sensor may be embedded in the wall of the vacuum globe to measure temperature of the globe at the treatment site. Camera 322 may be mounted with a lens projecting through the vacuum globe, preferably at the side of the globe away from where water is sprayed 120. The catheter may have a smooth outer surface so that the catheter can be easily be rotated, to alternate between camera view and then a touch of the cooling surface of the vacuum globe.

Conditions that may be treated include diseases of the esophagus such as esophageal cancer or Barrett's esophagus, diseases of the respiratory tract, diseases of the stomach or intestine or rectum.

V. EMBODIMENTS

An object or space may be cooled by placing the exterior surface of a cooling wall of a vacuum chamber against the object or space; spraying water from a mister into the vacuum chamber or against the cooling wall; maintaining vacuum in the vacuum chamber sufficient to cause accelerated evaporation of the water and cooling of the cooling wall to a temperature desired for cooling of the object.

An apparatus for cooling an object or space, may include a vacuum chamber with a cooling wall designed to be placed against the object or space to be cooled; a water spray designed to spray water into the vacuum chamber or against the cooling wall; and apparatus designed to maintain vacuum in the vacuum chamber sufficient to cause accelerated evaporation of the water and cooling of the cooling wall to a temperature desired for cooling of the object or space.

A patient may be treated by providing a vacuum chamber against tissues of the patient for which cooling is desired for treatment; spraying water from a mister into the vacuum chamber or against a cooling wall of the vacuum chamber; and maintaining vacuum in the vacuum chamber sufficient to cause accelerated evaporation of the water and cooling to a temperature desired for cooling of tissues of the patient.

Apparatus for treating a patient may include a vacuum chamber having a cooling wall designed to be placed against tissues of the patient for which cooling is desired for treatment; a water spray designed to spray water into the vacuum chamber; and maintaining vacuum in the vacuum chamber sufficient to cause accelerated evaporation of the water and cooling to a temperature desired for cooling of tissues of the patient.

A refrigeration device may include a thermally-conductive platen, possibly connected to a set of cooling fins; a vacuum bell sealed to the thermally conductive platen; a spray device mounted to spray water onto the thermally-conductive platen; a tank fluidly connected to the spray device to supply liquid to the spray device; a source of vacuum designed to cool the platen by drawing vacuum to accelerate evaporation of the water; an electronic computer programmed to obtain readings from temperature sensors, and based on those readings, to provide control signals to the water spray and to control vacuum pressure to achieve a level of evaporative cooling at the platen effective to induce a desired cooling of the platen; a device, such as a fan, to direct a flow of air across the platen and cooling fins; to induce a cooling of a selected region within the refrigeration device; a condenser to convert the coolant from vapor phase to liquid phase; a fluid connection from the source of vacuum to the condenser; a fluid connection from the condenser to the tank that supplies liquid to the spray device.

A device for medical or other therapeutic cooling of selected regions of a patient using vacuum-induced evaporative cooling of a liquid medium may include a conformal, highly thermal conductive platen for thermal contact with a region of tissue that is desired to be cooled, coated with a thin layer of a non-metallic release material to prevent sticking by freezing; a vacuum bell sealed to the thermally conductive platen; a vacuum seal between the chamber and the thermally conductive platen; a spray device mounted to spray water into the chamber onto the thermally-conductive platen; a source of vacuum connected to the chamber designed to cool the platen by drawing vacuum to accelerate evaporation of the water; an air inlet; a three-way valve assembly between the vacuum pump and air inlet to the chamber; a set of thermal sensors mounted within the thermally conductive platen; an exhaust of the vapor to the exterior of the desired cooled region; a device to generate a column of air across the conductive platen; an electronic computer programmed to obtain readings from temperature sensors, and based on those readings, to provide control signals to the water spray and to control vacuum pressure to achieve a level of evaporative cooling at the platen effective to induce a therapeutic result in a patient.

An air-conditioning device may include: a thermally-conductive platen connected to a set of cooling fins; a vacuum bell sealed to the thermally conductive platen; a spray device mounted to spray water onto the thermally-conductive platen; a tank fluidly connected to the spray device to supply liquid to the spray device; a source of vacuum designed to cool the platen by drawing vacuum to accelerate evaporation of the water; an electronic computer programmed to obtain readings from temperature sensors, and based on those readings, to provide control signals to the water spray and to control vacuum pressure to achieve a level of evaporative cooling at the platen effective to induce a desired cooling of the platen; a device, such as a fan, to direct a flow of air across the platen and cooling fins; to induce a cooling of a selected region of a room or enclosure; a condenser to convert the coolant from vapor phase to liquid phase; a fluid connection from the source of vacuum to the condenser; and a fluid connection from the condenser to the tank that supplies liquid to the spray device.

A method for cooling of selected regions of an enclosure using vacuum-induced evaporative cooling of a liquid medium may include: placing a highly thermally-conductive platen of a vacuum chamber against the region, the vacuum chamber having a vacuum bell connected to the thermally conductive platen, with a vacuum seal between the chamber and the thermally conductive platen; spraying water onto the platen via a spray device facing into the chamber; applying vacuum to the chamber, and exhausting the vapor to the exterior of the desired cooled region; receiving temperature readings from a set of thermal sensors mounted within the thermally conductive platen; generating a column of air across the conductive platen.

Specific instances may include the following features, singly or in any combination. The vacuum chamber may be formed as a vacuum bell sealed against flesh of the patient. The vacuum chamber may be formed as an enclosed volume having a cooling wall at one side, and the cooling wall is placed in physical contact with the tissues of the patient.

The conductive platen may be aluminum. The non-metallic material in contact with the tissue may prevent adhesion and tissue damage during the cooling process. The spray device may be mounted within a chamber attached to a thermally conductive material. The liquid medium may be water. The liquid medium may be saline. The liquid medium may be sodium chloride solution. The liquid medium may be calcium chloride solution. The solution level may be chosen to provide a selected liquid freezing temperature. The vacuum within the chamber may induce vaporization of the liquid from the surface of the conductive material. The vacuum application may be controlled by a valve assembly. The target temperature may be chosen to disrupt lipid-rich cells. The target temperature may be chosen to not damage the tissue skin surface. The cooling may be selected to provide analgesic effects to a desired region of the body. The cooling may be selected to ablate goblet cells. The cooling may be selected to restore normal epithelial cells. The cooling may be selected to freeze undesired gastrointestinal cells. The cooling may be selected to ablate undesired benign cells. The cooling may be selected to ablate malignant cells. The cooling may be selected to restore normal gastrointestinal cells. The cooling may be selected to provide skin lightening, i.e., hypopigmentation, to desired regions of the body. Electrical power for the system may be provided by the use solar energy converted to electricity by solar cells.

For clarity of explanation, the above description has focused on a representative sample of all possible embodiments, a sample that teaches the principles of the invention and conveys the best mode contemplated for carrying it out. The invention is not limited to the described embodiments. Well known features may not have been described in detail to avoid unnecessarily obscuring the principles relevant to the claimed invention. Throughout this application and its associated file history, when the term "invention" is used, it refers to the entire collection of ideas and principles described; in contrast, the formal definition of the exclusive protected property right is set forth in the claims, which exclusively control. The description has not attempted to exhaustively enumerate all possible variations. Other undescribed variations or modifications may be possible. Where multiple alternative embodiments are described, in many cases it will be possible to combine elements of different embodiments, or to combine elements of the embodiments described here with other modifications or variations that are not expressly described. A list of items does not imply that any or all of the items are mutually exclusive, nor that any or all of the items are comprehensive of any category, unless expressly specified otherwise. In many cases, one feature or group of features may be used separately from the entire apparatus or methods described. Many of those undescribed alternatives, variations, modifications, and equivalents are within the literal scope of the following claims, and others are equivalent. The claims may be practiced without some or all of the specific details described in the specification. In many cases, method steps described in this specification can be performed in different orders than that presented in this specification, or in parallel rather than sequentially, or in different computers of a computer network, rather than all on a single computer.

The invention claimed is:

1. Apparatus for treating a patient, comprising:
   a vacuum chamber having a cooling wall designed to be placed in thermal contact tissues of the patient for which cooling is desired for treatment;
   a water sprayer designed to spray water as a coolant against the cooling wall of the vacuum chamber; and
   a vacuum pump and control designed to maintain vacuum at or below 0.02 atm, in the vacuum chamber, the maintained vacuum being below ambient pressure and sufficient to cause accelerated evaporation of the water and cooling to a temperature desired for cooling of tissues of the patient.

2. The apparatus of claim 1, further comprising:
   valves designed to alternatively connect the vacuum chamber to vacuum suction or to vent the vacuum chamber to inlet air.

3. A method of treating a patient, comprising the steps of:
   providing a vacuum chamber in thermal contact with tissues of the patient for which cooling is desired for treatment;
   spraying water from a mister into the vacuum chamber or against a cooling wall of the vacuum chamber;
   maintaining vacuum below 0.02 atm, in the vacuum chamber, sufficient to cause accelerated evaporation of the water and cooling to a temperature desired for cooling of tissues of the patient.

4. The method of claim 3, wherein:
   the vacuum chamber is formed as a vacuum bell sealed against flesh of the patient.

5. The method of claim 3, wherein:
   the vacuum chamber is formed as an enclosed volume having a cooling wall at one side, and the cooling wall is placed in physical contact with the tissues of the patient.

6. The method claim 3, wherein:
   the vacuum chamber is formed as a vacuum bell sealed to a flat thermally conductive platen, the platen designed to be placed in thermal contact with the tissue, object, or space.

7. The method of claim 6, wherein:
   the platen is coated with a non-metallic nonstick release material designed to prevent adhesion and resultant tissue damage resulting from freezing of the tissue to be cooled or water between the tissue and the platen.

8. The method claim 3, wherein:
   the water has in solution an electrolyte chosen to depress freezing point of the water to a desired temperature.

9. The method claim 3, wherein:
   the tissue to be cooled is adipose tissue of the patient.

10. The method claim 3, wherein:
    the cooling of the tissue is designed to reduce pain.

11. The method of claim 3, wherein:
    the cooling of the tissue is designed to lighten skin and/or to reduce hypopigmentation.

12. The method of claim 3, wherein:
    the tissue to be cooled is in a gastrointestinal tract of the patient.

13. The method of claim 3, wherein the tissue to be cooled is in a respiratory tract of the patient.

14. The method claim 13, wherein:
    the tissue to be cooled includes goblet cells to be disrupted.

15. The method claim 3, wherein:
    the tissue to be cooled includes malignant cells to be ablated.

16. The method claim 3, wherein:
the tissue to be cooled includes undesired benign cells that are selectively sensitive to cold, and the cooling is designed to disrupt these undesired benign cells.

17. The method of claim 3, further comprising the step of:
by way of valves, alternatively connecting the vacuum chamber to vacuum suction or venting the vacuum chamber to inlet air.

18. Apparatus for treating a patient, comprising:
a vacuum chamber having a cooling wall designed to be placed in thermal contact with tissues of the patient for which cooling is desired for treatment;
a water sprayer designed to spray water as a coolant against the cooling wall of the vacuum chamber; and
a vacuum pump and control designed to maintain vacuum at or below 0.02 atm in the vacuum chamber sufficient to cause accelerated evaporation of the water and cooling to a temperature desired for cooling of tissues of the patient.

19. The apparatus of claim 18, wherein:
the vacuum chamber is formed as a vacuum bell sealed against flesh of the patient.

20. The apparatus of claim 18, wherein:
the vacuum chamber is formed as an enclosed volume having a cooling wall at one side, and the cooling wall is placed in physical contact with the tissues of the patient.

21. The apparatus of claim 20, wherein:
the platen is coated with a non-metallic nonstick release material designed to prevent adhesion and resultant tissue damage resulting from freezing of the tissue to be cooled or water between the tissue and the platen.

22. The apparatus claim 18, wherein:
the tissue to be cooled is adipose tissue of the patient.

23. The apparatus claim 18, wherein:
the cooling of the tissue is designed to reduce pain.

24. The apparatus of claim 18, further comprising:
valves designed to alternatively connect the vacuum chamber to vacuum suction or to vent the vacuum chamber to inlet air.

25. An apparatus for cooling an object or space, comprising:
a vacuum chamber with a cooling wall designed to be placed in thermal contact with the object or space to be cooled;
a water spray designed to spray water as a coolant into the vacuum chamber or against the cooling wall;
apparatus designed to maintain vacuum at or below 0.02 atm, in the vacuum chamber, sufficient to cause accelerated evaporation of the water and cooling of the cooling wall to a temperature desired for cooling of the object or space.

26. The apparatus claim 25, wherein:
the vacuum chamber is formed as a vacuum bell sealed to a flat thermally conductive platen, the platen designed to be placed in thermal contact with the tissue, object, or space.

27. The apparatus claim 25, wherein:
the vacuum chamber includes one or more thermal sensors; and
the maintaining of vacuum is controlled by a computer designed to obtain thermal data from the one or more thermal sensors, and to control one or more of water flow rate, vacuum pressure, and electrolyte solution, to control for a desired temperature and/or rate of cooling, and/or to correct for various confounders in thermal flow into the vacuum chamber.

28. The apparatus claim 25, wherein:
the space to be cooled is an enclosed space to be cooled to refrigeration or freezing temperatures.

29. The apparatus claim 25, wherein:
the space to be cooled is a room to be cooled to air conditioning temperatures.

30. The apparatus of claim 25, further comprising:
valves designed to alternatively connect the vacuum chamber to vacuum suction or to vent the vacuum chamber to inlet air.

* * * * *